United States Patent [19]

Varga et al.

[11] Patent Number: 5,264,225

[45] Date of Patent: Nov. 23, 1993

[54] SILICON-CONTAINING ENVIRONMENT-PROTECTIVE AGENT ADSORBING RADIOACTIVE METAL ISOTOPES AND TOXIC HEAVY METALS AND A PHARMACEUTICAL COMPOSITION CONTAINING SAME

[75] Inventors: László Varga, Budapest; Mihály Törocsik, Tószeg; Bálint L. Sztanyik, Budapest, all of Hungary

[73] Assignees: Argomen Agrarmenedzseri Kft., Szolnok; Orszagos "Frederic Joliot-Curie" Sugarbiologiai es Sugar-Egeszsegugyi Kutato Intezet; Magyar Kulkereskedelmi Bank Rt., both of Budapest, all of Hungary

[21] Appl. No.: 635,635

[22] PCT Filed: Mar. 21, 1990

[86] PCT No.: PCT/HU90/00020

§ 371 Date: Dec. 20, 1990

§ 102(e) Date: Dec. 20, 1990

[87] PCT Pub. No.: WO90/11143

PCT Pub. Date: Oct. 4, 1990

[30] Foreign Application Priority Data

Mar. 24, 1989 [HU] Hungary .............. 1511/89

[51] Int. Cl.$^5$ .................. A61K 33/08; C01B 33/12
[52] U.S. Cl. .................. 424/684; 424/724; 514/917; 514/951; 252/184
[58] Field of Search .............. 252/184; 424/684, 724; 514/917, 951

[56] References Cited

U.S. PATENT DOCUMENTS

| | | | |
|---|---|---|---|
| 3,449,492 | 6/1969 | Jensen | 424/684 |
| 3,687,680 | 8/1972 | Krchnavi et al. | 424/684 |
| 4,563,479 | 1/1986 | Feuer et al. | 514/917 |
| 4,610,883 | 9/1986 | Laurent et al. | 424/684 |
| 4,698,335 | 10/1987 | Spillert et al. | 514/917 |

FOREIGN PATENT DOCUMENTS

| | | | |
|---|---|---|---|
| 3228425 | 2/1984 | Fed. Rep. of Germany | 424/684 |
| 3337335 | 5/1985 | Fed. Rep. of Germany | |
| 2397189 | 2/1979 | France | 424/684 |
| 0040923 | 6/1973 | Japan | 424/684 |
| 3020437 | 2/1978 | Japan | 424/684 |

OTHER PUBLICATIONS

Chemical Abstracts, vol. 100, No. 6, Feb. 6, 1984, "Floatability of Zeolite with dodecylammonium acetate", Horioka et al.
Chemical Abstracts, vol. 77, No. 4, Jul. 24, 1972, "Polyethylene powder as a radioactive gas-absorbing agent," Danno et al.

Primary Examiner—Richard D. Lovering
Assistant Examiner—Joseph D. Anthony
Attorney, Agent, or Firm—Michael N. Meller

[57] ABSTRACT

The invention relates to an environment-protective agent consisting of silicon-containing minerals for adsorbing radiactive metal isotopes and toxic heavy metals, which comprises as silicon-containing minerals with a particle size of 0.001 to 0.5 mm; a natural diatomaceous earth and at least two natural zeolite minerals of the general formula $$M_xO.Al_2O_3.YSiO_2.7H_2O$$

wherein
M stands for sodium, potassium or calcium;
x is a number between 1 and 2 inclusive of both extreme values;
Y is 3 or 10; and
Z is 6 or 7 treated by dilute acid, washed to neutral, dried to a constant weight at a temperature up to 115°0 C. and then heat-treated at 150° to 350° C., preferably at 250° C., where the amount of each mineral ingredient independently of each other is at least 0.1% by weight up to 99.8% by weight calculated to the total weight of the agent.

The invention further relates to pharmaceutical compositions and animal foods containing the above agent according to the invention as active ingredient.

3 Claims, No Drawings

SILICON-CONTAINING ENVIRONMENT-PROTECTIVE AGENT ADSORBING RADIOACTIVE METAL ISOTOPES AND TOXIC HEAVY METALS AND A PHARMACEUTICAL COMPOSITION CONTAINING SAME

The invention relates to a silicon-containing agent consisting of natural minerals with a loose structure and large surface, which can be used to decrease the load induced by radioactive isotopes and toxic heavy metals as well as a pharmaceutical composition containing the same agent as active ingredient.

Due to the continuously extending activities of the nuclear industries as well as to an increase in other industrial works, a sudden and unexpected occurrence of high amounts of toxic heavy metals and radioactive isotopes endangering man and his environment, mainly after any disaster, should be taken into account. This can be a natural disaster or an industrial accident, e.g. the explosion of a nuclear reactor. Thus, one has to prepare himself for such cases and to find the means to reduce most effectively the occurring damages.

In the course of explosion of a nuclear power plant the radioactive isotopes get into the a , e.g. as gases or vapours or in a form bound to a liquid or solid carrier. From the air-space they get onto the soil, in the water, plants and indirectly or directly into the animals or men. It is commonly known that, depending on their amount, they can cause death, too. Thus, it is a very important task to collect these harmful isotopes and to remove same rapidly from the living beings or from the contaminated environment, respectively. The present invention has been developed in order to solve this task. Before the detailed description of the invention, the technical background will briefly be summarized by examples referring to the antecedents.

It has long been observed that diatomaceous earth, a natural loosely structured mineral essentially consisting of $SiO_2$, which had been formed from the rests of minute, deceased living organisms, is capable to adsorb radioactive isotopes on its surface [J. Oglaza et. al.: Nukleonika 10, 519-522 (1965)].

It is also known that zeolite, a porous natural mineral with a solid skeleton but large surface is also able to bind metal ions, even radioactive metal isotopes. Based on this ability, it has been used for purifying water (European patent application No. 0,175,956 made open to public inspection).

According to Matsumura, Takashi, Ishiyama, Toshio (Radiation Center of Osaka Prefecture, Sakai): Annu. Rep. Radiat. Center Osaka Prefect. (Mar 1975), Vol. 15, p. 35-37 the decontamination property of the so-called manganese-zeolite, made from montmorillonite was studied. Each radioactive material was hardly removed at the contact time less than 20 min.

The selective removal and fixation of Cs and Sr have been studied in zeolite A and chabazite. The initial rate of Cs adsorption was fairly fast in chabazite but the adsorption ratio reached 100% within a few hours. Adsorption ratio of Sr in binderless A zeolite reached almost 100% after 15 h. (Mimura, Hitoshi, Kanno, Takuji: J. Nucl. Sci. Technol. (Tokyo) 1985 Vol. 22 (4) p. 284-291. Consequently, said zeolites are not really suitable for a quick and effective adsorption.

A high number of experiments was carried out with the above minerals to find an agent being able to bind harmful ions even in a high dilution in a rapid, effective and reliable manner and thereby to cure or improve the living or inanimate loaded environment.

It has been observed that the minerals mentioned above were particularly effective when their number in the agent was higher than one.

It has furthermore been recognized that, though these natural minerals were very good adsorbents for the harmful metals, their effectivity was surprisingly enhanced by a pretreatment before being composed to an agent.

For pretreatment the natural minerals are ground to a particle size of 0.001 to 0.5 mm and treated by a dilute acid, preferably hydrochloric acid solution. The dilute aqueous acid solution exerts also a purifying, loosening activity increasing the surface. The solution used for treatment may be an aqueous solution of 1 to 10% by weight, preferably 3% by weight. The ratio of the solution to the solid is usually 20 ml of solution related to 1 g of solid.

The mineral treated by using a diluted aqueous acid is washed to neutral with deionized water. Usually, this means three washings requiring 30 minutes.

Subsequently, the wet neutral mineral is further treated in a physical way: it is maintained at 100° to 115° C. in an inert atmosphere, preferably in air, then heat-treated at 150° to 300° C. for 3 hours.

The experimental samples, which made possible to develop the active agent, consist of minerals pretreated in the above manner, preferably at 250° C.

It has been found that diatomaceous earth should necessarily be present in the agent. Its' amount may be varied, but even a trace of the composition surprisingly increases the effectivity of the composition whereas it may also represent the main bulk of the agent.

In addition at least two of the zeolite minerals of the general formula $$M_xO \cdot Al_2O_3 \cdot YSiO_2 \cdot ZH_2O$$

should be present. In the above formula

M stands for sodium, potassium or calcium;

x is a number between 1 and 2 inclusive of both extreme values;

Y is 3 or 10; and

Z is 6 or 7.

The quantity of the mineral of general formula $M_xO \cdot Al_2O_3 \cdot YSiO_2 \cdot ZH_2O$ in the agent may similarly vary; it may represent the main bulk of it or one of the minerals may be present in a nearly trace amount. However, this amount should unconditionally be present, otherwise the expected effect, i.e. the rapid adsorption fails to come about.

The agent able to bind the toxic heavy metals and radioactive isotopes can be prepared from at least three kinds of natural, silicon-containing mineral particles pretreated in the above manner.

Based on these observations an agent has been developed, which comprises as silicon-containing minerals of a particle size of 0.001 to 0.5 mm: a natural earth and at least two natural zeolite minerals of the general formula $$M_xO \cdot Al_2O_3 \cdot YSiO_2 \cdot ZH_2O$$

wherein

M stands for sodium, potassium or calcium;

x is a number between 1 and 2 inclusive of both extreme values;

Y is 3 or 10; and

Z is 6 or 7 treated with a dilute acid, washed with deionized water to neutral, dried at a temperature not higher than 115° C. and then heat-treated at 150° to 350° C. and where the amount of each ingredient independently of each other is at least 0.1% by weight and at most 99.8% by weight calculated for the total weight of the agent.

A preferable agent according to the invention contains 15% by weight of diatomaceous earth whereas the bilance consists of zeolite mineral where the mineral ingredient wherein Y is 10 and Z is 7, conveniently represents 45 to 50% by weight.

The particle size of the ingredients is preferably between 0.09 mm and 0.25 mm.

It should be noted that, being of natural character, the mineral ingredients of the agent according to the invention contain also accompanying materials being inert concerning the invention. An ingredient is useful for the invention when it contains at least 25% by weight of the required mineral in the case of zeolite and at least 40% by weight in the case of diatomaceous earth.

The agent according to the invention can be used with a great advantage for decreasing the toxic heavy metal load such as cadmium and lead load of soils. These metals get into the soil among others from the air or artificial fertilizers or sewage sludge, then they are transferred into the plants and via the plants into the broader living environment. The agent according to the invention binds at least twice but rather three times higher heavy metal load than the soil in itself does.

The agent according to the invention can furthermore be used with good efficiency to bind radioactive isotopes falling onto the soil or plants as well as to remove (separate) the radioactive isotopes from the soil or the plant surface.

Finally, the agent according to the invention can also be used for reducing the radiation load of other living beings in addition to the plants.

Mice and rats internally contaminated by radioactive isotopes were fed with a food containing the agent according to the invention.

It should be noted that the mutual ratio of the mineral ingredients of the agent according to the invention cannot be selected so freely as in the fields of utilization discussed above. When a curative effect is desired by using the agent according to the invention, then the amount of zeolites should be predominant by all means; here, the diatomaceous earth content of the mineral mixture used as agent according to the invention should not exceed 1% by weight, preferably it amounts to 0.5% by weight. The mutual ratio of zeolites can be varied without any restriction ranging from a preponderant quantity to a trace amount, however, the ratio of the two zeolite ingredients is preferably between 1:0.9 and 0.9:1.1.

From the results of our experiments calculations concerning the changes in the radiation load of the animals were carried out. Normal, pregnant and new-born mice and rats were used as test animals.

In these experiments, a food containing 5% by weight of agent according to the invention was used for feeding the animals. The agent according to the invention contained 55% by weight of $M_xO.Al_2O_3.10SiO_2.7H_2O$, 44% by weight of $M_xO.Al_2O_3.3SiO_2.6H_2O$ and 1% by weight of diatomaceous earth calculated for the total weight of the mineral mixture.

The normal animals received for 3 days before the internal isotope contamination and for 6 days after the contamination the food prepared with the formula defined above (i.e. a pretreatment of 3 days and a posttreatment of 6 days were carried out).

The pregnant animals were treated according to the same time sequence as described above but they also received a food containing only one of the zeolite minerals, i.e. $M_xO.Al_2O_3.10SiO_2.6H_2O$ similarly in an amount of 5% by weight. (The control group was naturally only fed with a food containing no agent according to the invention.)

The results are given in relation to the control group by considering the radiation load of the control group as 100% and determining the radiation load of the animals fed with the food containing the agent of the invention in relation to that of the control group.

The radiation load of normal animals was reduced to 40–50% as mentioned above.

The radiation load of pregnant animals fell to 28–30% by feeding them with a food containing only one kind of zeolite; and to 20–23% by feeding them with a food containing the active agent according to the invention described above.

The measurements show the decrease in the radiation load to be even more obvious on pregnant animals; also, it can clearly be seen that, contrarily to the use of a single zeolite, an additional decrease in the radiation load was achieved by using the agent according to the invention.

Based on this recognition an oral pharmaceutical composition has been developed which comprises pharmaceutically acceptable carriers, preferably water or fodder or both together with an agent comprising a natural diatomaceous earth and at least two natural zeolite minerals of the general formula

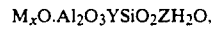

$$M_xO.Al_2O_3YSiO_2ZH_2O,$$

wherein

M stands for sodium, potassium or calcium;

x is a number between 1 and 2 including both extreme values;

Y is 3 or 10; and

Z is 6 or 7 treated by dilute acid, washed with deionized water to neutral, dried to constant weight at a temperature not exceeding 115° C., subsequently heat-treated at 150° to 350° C. and ground to a particle size of 0.001 to 0.5 mm, suitably to a particle size of 0.09 to 0.25 mm and where the amount of each zeolite ingredient is independently of each other at least 0.1% by weight up to 99.8% by weight calculated to the total weight of the agent whereas the amount of diatomaceous earth is up to 1% by weight calculated to the total weight of the agent.

According to a preferred embodiment of the process according to the invention a pharmaceutically acceptable carrier is mixed with an agent according to the invention, which contains 0.5% by weight of diatomaceous earth and 45 to 50% by weight of natural zeolite mineral of the general formula $M_xO.Al_2O_3.10SiO_2.7H_2O$.

An even more preferred pharmaceutical composition can be prepared by mixing as active ingredient 1 to 10% by weight of the agent according to the invention with a particle size of $0.1 \pm 0.02$ mm with a carrier, preferably with an animal fodder.

The activity of the pharmaceutical composition according to the invention was investigated on rats.

The animals were fed for 24 hours with a food containing an agent according to the invention which contained 5 to 0.5% by weight of diatomaceous earth and 50% by weight of $M_xO.Al_2O_3.3SiO_2.6H_2O$ with a particle size of $0.25\pm0.05$ mm. The animals received the agent in an amount of 4 g/kg of body-weight. The $^{134}Cs$, $^{85}Sr$ or $^{144}Ce$ isotopes were introduced through a gastric tube into the gastrointestinal tract of the animals. The evacuated activities were compared to those of the control group. It was observed that this value was doubled or even tripled.

When no pre-feeding was used but the agent of the above composition was administered 30 minutes after the internal isotope contamination, the evacuated amount was doubled.

This is important concerning the decrease in the radiation load of living beings. Thus, it is preferred to store a certain amount of such composition for both the specially qualified underofficials as well as the civilian population.

A number of laboratory investigations was carried out by using the agent according to the invention, some of which will be illustrated in the following non-limiting Examples.

EXAMPLE 1

To an aqueous caesium chloride solution of 10 µg/ml concentration $^{134}Cs$ isotope is mixed. The volume of the solution sample is 50 ml of a pH value of $7\pm0.5$. To 1 ml of the caesium chloride solution 400 mg of the mineral to be tested are weighed in order to determine the extent of binding the isotope as a function of the contact time (time of reaction). The results are summarized in Table 1, where the numerical values mean the percentage of the bound isotope ions.

TABLE 1

| Mineral | Contact time (min) | | | |
|---|---|---|---|---|
| | 1 | 20 | 45 | 90 |
| $M_xO.Al_2O_3.3SiO_2.6H_2O$ | 96.4 | 97.23 | 97.67 | 98.64 |
| $M_xO.Al_2O_3.10SiO_2.7H_2O$ | 91.14 | 91.94 | 93.12 | 95.39 |
| Diatomaceous earth | 94.74 | 97.26 | 97.85 | 97.88 |

EXAMPLE 2

Example 1 is followed, except that the contact (reaction) time lasts 20 minutes. The aim of this examination is to determine the percentage of the extent of the isotope binding as a function of the mineral/solution ratio. The results are summarized in Table 2, where the numerical values mean the percentage of the bound isotope ions.

TABLE 2

| Mineral | Mineral/solution ratio (mg/ml) | | | | |
|---|---|---|---|---|---|
| | 20 | 40 | 100 | 200 | 500 |
| $M_xO.Al_2O_3.3SiO_2.6H_2O$ | 41.47 | 38.89 | 62.23 | 78.72 | 92.46 |
| $M_xO.Al_2O_3.10SiO_2.7H_2O$ | 32.68 | 50.23 | 69.80 | 80.09 | 85.76 |
| Diatomaceous earth | 53.25 | 53.36 | 89.95 | 94.80 | 96.16 |

EXAMPLE 3

Example 1 is followed, except that the caesium ion concentration of the caesium chloride solution is 20 µg/ml; and the mineral mixture/solution ratio is 40 mg/ml. The tested mineral mixture consists of 45% by weight of $M_xO.Al_2O_3.3SiO_2.6H_2O$, 45% by weight of $M_xO.Al_2O_3.10SiO_2.7H_2O$ and 10% by weight of diatomaceous earth. The aim of this examination is to determine the extent of isotope binding as a function of the contact time. The results are summarized in Table 3, where the numerical values mean the percentage of the bound ions.

TABLE 3

| Mineral | Contact time (min) | | |
|---|---|---|---|
| | 1 | 20 | 60 |
| The mixture described above | $90 \pm 7.6$ | $93.1 \pm 3.8$ | $95.8 \pm 2.8$ |

On comparison of these values to the corresponding values of Table 2, the effectivity of the mixture is obvious in relation to that of the separate ingredients.

EXAMPLE 4

A solution containing $^{144}Ce$ ions is contacted with an untreated mineral or treated with an acid Dr with acid and heat. The acid treatment is performed by using 20 ml of a hydrochloric acid solution of 3% by weight for 1 g of mineral. The mineral washed to neutral is dried to a constant weight at 110° C. and heat-treated at 200° C. for 3 hours.

The amount of the ions bound from the solution is measured and given as weight percentage in Table 4. The calculation is based on the total amount of the cerium isotope introduced.

TABLE 4

| Contact time (min) | Mineral | | | | | | | | |
|---|---|---|---|---|---|---|---|---|---|
| | $M_xO.Al_2O_3.10SiO_2.7H_2O$ | | | $M_xO.Al_2O_3.3SiO_2.6H_2O$ | | | Diatomaceous earth | | |
| | | Treated | | | Treated | | | Treated | |
| | Untreated | with acid | with acid and heat | Untreated | with acid | with acid and heat | Untreated | with acid | with acid and heat |
| 1 | 62.6 | 96.8 | 95.1 | 85.6 | 97.3 | 94 | 93.3 | 98.5 | 94.1 |
| 5 | 88 | 94.3 | 95.8 | 83.4 | 95.3 | 95.5 | 91.3 | 94.4 | 96.7 |

It is obvious from Table 4 that the acid treatment is unambiguously positive and is not deteriorated by the heat-treatment. This latter is required to make the material sterile.

EXAMPLE 5

The binding of lead and cadmium ions was also studied. The following concentration series was arranged from the starting solution:

| Pb (ppm) | Cd (ppm) |
|---|---|
| 5000 | 200 |
| 2000 | 50 |
| 500 | 20 |

| Pb (ppm) | Cd (ppm) |
|---|---|
| 200 | 5 |
| 50 | 2 |

After adding 1 g of the mineral to be tested to 20 ml of the solution (and thus obtaining a ratio of 1 g of solid to 20 ml of solution) the mixture is shaken for 24 hours, then the solid is separated from the liquid phase and the remaining quantity of lead or cadmium, respectively is measured. Each experiment is carried out in several repetitions. The mean values of measurements with the limits of error are summarized in Tables 5 and 6.

TABLE 5

| Mineral | Pb(added)(ppm) | Pb(residual)(ppm) |
|---|---|---|
| An agent containing 67 parts of $M_xO.Al_2O_3.3SiO_2.6H_2O$ and 27 parts of $M_xO.Al_2O_3.10SiO_2.7H_2O$ supplemented up to 100 parts with diatomaceous earth | 50 | 0 |
| | 200 | 0 |
| | 500 | 8.5 ± 10 |
| | 2000 | 905 ± 299 |
| | 5000 | 3510 ± 479 |

TABLE 6

| Mineral | Cd(added)(ppm) | Cd(residual)(ppm) |
|---|---|---|
| An agent containing 67 parts of $M_xO.Al_2O_3.3SiO_2.6H_2O$ and 30 parts of $M_xO.Al_2O_3.10SiO_2.7H_2O$ supplemented up to 100 parts with diatomaceous earth | 2 | 0 |
| | 5 | 0 |
| | 20 | 0.75 ± 0.96 |
| | 50 | 10.75 ± 2.99 |
| | 200 | 72 ± 17 |

It is obvious from the Examples and from own observations that the selected minerals prepared by using the process according to the invention are excellent adsorbents per se; but, this effect is synergistically increased by using a mixture thereof (see Examples 3 and 4).

On contacting e.g. an isotope-contaminated liquid with an agent containing 15% by weight of diatomaceous earth and 50% by weight of $M_xO.Al_2O_3.10SiO_2.7H_2O$, a significant part of the total radioactive isotope amount was bound after 1 minute of contact, whereas practically the total amount was bound after 30 minutes.

The agent according to the invention can be used in all cases where the heavy metal content has to be reduced, first of all for improving soils or for binding the toxic metal content of the soil so that said metals cannot be taken up by water or plants.

The agent according to the invention can excellently be used for the treatment of wastes containing radioactive isotopes since the isotopes are extracted (removed) and strongly bound by the agent providing a safe further storage.

The pharmaceutical composition according to the invention also opens very advantageous prospects since its active ingredient (i.e. the agent according to the invention) is nontoxic and does not particularly load the human or animal organism but significantly decreases the radiation load of these organisms whereby a curative effect is achieved.

Natural zeolites were studied in detail from the point of view of animal fodders as well Castro, M. and Pastrana, M. have not found substantial difference in fodder utilization in piglet experiments when adding 3-9% by weight of zeolite to the fodder. (Occurrence, properties and utilization of natural zeolites. Ed. Akademia, Budapest, 1988 p. 721).

Smith, T. K. has not observed any change in raw fibre digestion and protein metabolism (J. Anim. Sci. 50: 278 (1980)) when adding as much as 25% of zeolite to the fodder. According to our own observations young mice when fed with a fodder with 1-5% of zeolite for several months, showed an increase of weight and no change could be found in their general state, body temperature and blood picture compared to the control. A preferred daily dose is 2 to 10% by weight, preferably 5% by weight of the composition related to the food or animal fodder resp.

We claim:

1. Oral pharmaceutical composition for removing radioactive isotopes getting into the human organism, which comprises a pharmaceutically acceptable carrier selected from the group consisting of water animal food, and mixture thereof and, as therapeutically active ingredient, an agent comprising natural diatomaceous earth and at least two natural zeolite minerals of the general formula $$M_xO.Al_2O_3.YSiO_2.ZH_2O$$

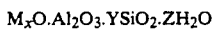

wherein

M is selected from the group consisting of sodium, potassium and calcium;

x is a number between 1 and 2 inclusive of both extreme values;

Y is 3 or 10; and

Z is 6 or 7 treated by dilute acid, washed to neutral, dried up to 115° C. and then heat-treated at 150° to 350° C., where the particle size is 0.001 to 0.5 mm and the amount of each zeolite ingredient is at least 0.1% by weight up to 99.8% by weight and the amount of diatomaceous earth is from 0.1 to 1% by weight calculated to the total weight of the agent.

2. An oral pharmaceutical composition as claimed in claim 1, which comprises as therapeutically active ingredient an agent containing 0.5% by weight of diatomaceous earth and 45 to 50% by weight of each of the two zeolite minerals of the general formula $M_xO.Al_2O_3.10SiO_2.7H_2O$ each with a particle size of 0.1±0.02 mm wherein 5-10% of the active ingredient is admixed with 90 to 95% by weight of animal food as a carrier, calculated to the total weight of the composition.

3. An oral pharmaceutical composition according to claim 1, wherein the amount of diatomaceous earth is about 0.5% by weight.

* * * * *